United States Patent [19]

Theisler

[11] Patent Number: 4,953,568
[45] Date of Patent: Sep. 4, 1990

[54] ADJUSTABLE THUMB BRACE

[76] Inventor: Charles W. Theisler, 1749 S. Raccoon Rd., Austintown, Ohio 44515

[21] Appl. No.: 486,871

[22] Filed: Mar. 1, 1990

[51] Int. Cl.$^5$ .............................................. A61F 13/00
[52] U.S. Cl. ..................................... 128/878; 128/879; 128/880
[58] Field of Search ................ 128/880; 2/16, 21, 163

[56] References Cited

U.S. PATENT DOCUMENTS

| | | | |
|---|---|---|---|
| 1,568,668 | 1/1926 | Harrison | 128/880 |
| 1,733,933 | 10/1929 | Beltz | 128/880 |
| 1,929,318 | 10/1933 | Klosky | 128/880 |
| 2,074,113 | 3/1937 | Hovey | 128/880 |
| 2,225,986 | 12/1940 | Belknap | 128/880 |
| 2,429,563 | 10/1947 | Palutzke | 128/880 |
| 2,498,122 | 2/1950 | Haniuk | 128/880 |
| 2,523,606 | 9/1950 | Young | 128/90 |
| 4,062,540 | 12/1977 | Calentine | 2/21 |
| 4,519,097 | 5/1985 | Chappell, Jr. et al. | 2/16 |
| 4,638,511 | 1/1987 | Haack | 2/21 |
| 4,653,490 | 3/1987 | Eisenberg | 128/880 |
| 4,658,441 | 4/1987 | Smith | 2/16 |
| 4,689,828 | 9/1987 | Brewer | 2/21 |

Primary Examiner—Mickey Yu
Assistant Examiner—Charles H. Sam
Attorney, Agent, or Firm—Harpman & Harpman

[57] ABSTRACT

A flexible adjustable thumb brace to position and hold the thumb portion of a patient's hand so as to restrict movement and supply adequate support thereto. The thumb brace encompasses the patient's hand with a separate thumb engageable portion. Adjustment and support straps engage the brace and the thumb portion, stabilizing same against movement and further injury.

4 Claims, 1 Drawing Sheet

ADJUSTABLE THUMB BRACE

BACKGROUND OF THE INVENTION

1. Technical Field

This device relates to hand and thumb support structures that are engageable on the hand of a patient to protect or support the thumb in a predetermined fixed relationship to the hand to prevent further injury and assist the healing of an injured thumb.

2. Description of Prior Art

Prior Art devices of this type have relied on a variety of different glove like and strap configurations to define thumb restraints, see for example U.S. Pat. No. 2,074,113, U.S. Pat. No. 2,523,606 and U.S. Pat. No. 4,653,490.

In U.S. Pat. No. 2,074,113 a thumb or finger guard is disclosed which is characterized by a laced sleeve around the entire length of the thumb with a support strap extending therefrom. The support strap prevents the lace thumb engaging sleeve from coming off the thumb by restricting its upward movement.

U.S. Pat. No. 2,523,606 discloses a plastic knuckle support that has a rigid transparent contoured support piece that holds the thumb in a predetermined restrictive position. A two-part strap extends from the rigid support piece with an adjustable fastening means positioned on their respective free ends.

U.S. Pat. No. 4,653,490 shows a thumb restraint comprised of a glove configuration having a rigid preshaped retainer for insertion into the thumb portion of the glove. In an alternate form of the invention a two-part ribbon is wrapped around the thumb to support same with the free ends of the ribbons adjustably secured to one another on the patient's hand opposite the thumb.

SUMMARY OF THE INVENTION

A flexible adjustable thumb brace removably positioned on a thumb and palm portion of a patient's hand so as to encircle same for interconnected support. Support and adjustment straps independently adjust the thumb brace and the palm portion adjustably supporting the thumb portion by the movable overlapping incrementally of the thumb portion of the brace.

DESCRIPTION OF THE PREFERRED EMBODIMENT

Figure 1:
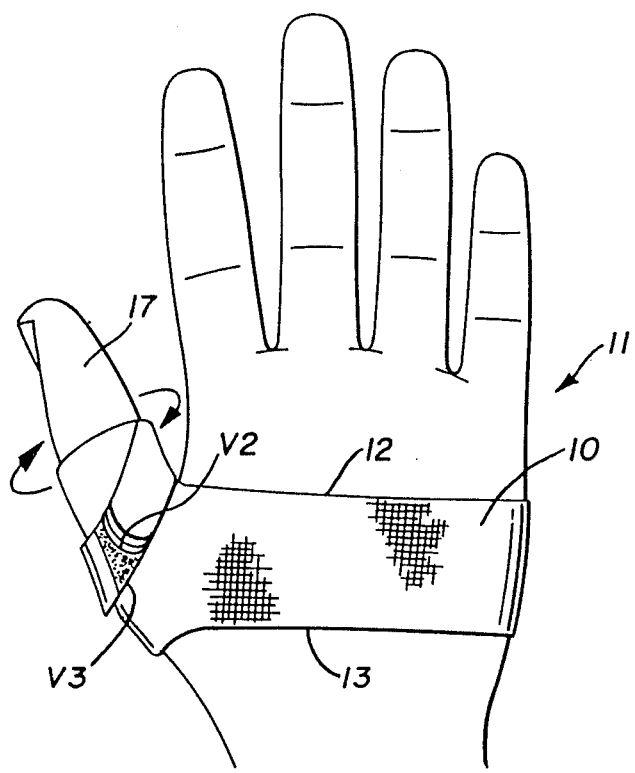
FIG. 1 is a front plan view of a palm side of a hand having the thumb restraint fully engaged thereon.
Figure 2:
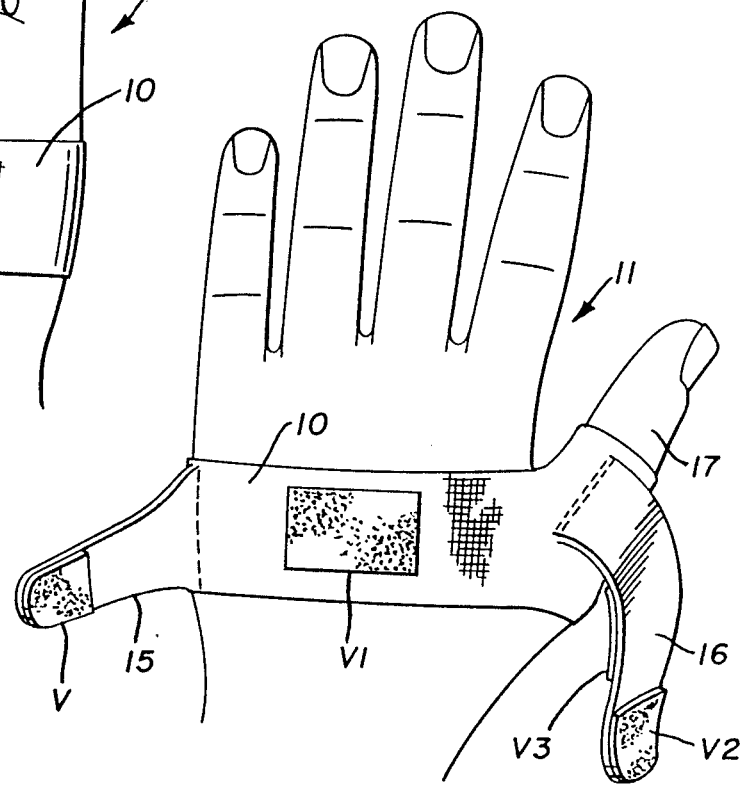
FIG. 2 is a back plan view of a hand showing the hand with the thumb restraint positioned thereon prior to full engagement.
Figure 3:
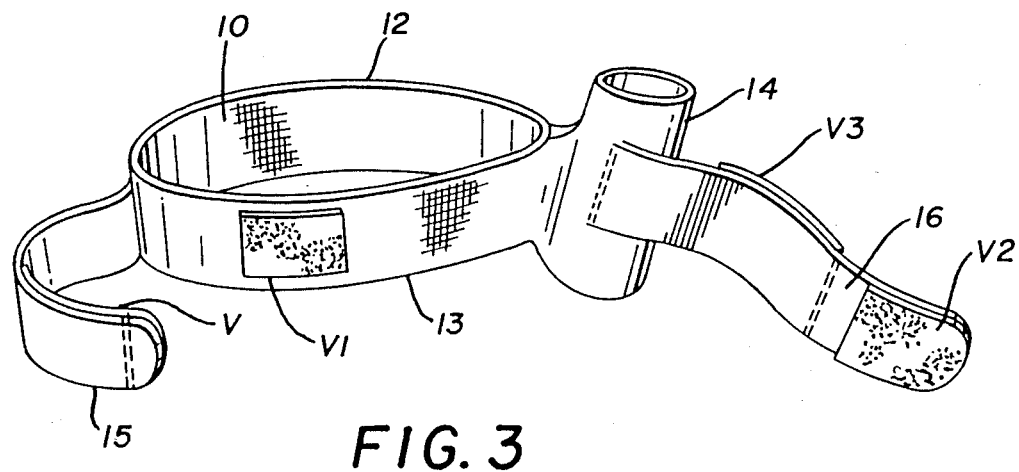
FIG. 3 is a perspective view of the thumb restraint by itself.

An adjustable thumb restraint can be seen in FIGS. 1, 2, and 3 of the drawings comprising a semiresilient annular band 10 having an overall outer dimension generally equal to or less than that of a patient's hand 11. The annular band 10 has upper and lower edge portions 12 and 13 defining a band of material therebetween. A thumb engaging portion 14 is secured to said annular band 10 and extends beyond both upper and lower edge portions 12 and 13 as best seen in FIG. 3 of the drawings.

The thumb engaging portion 14 defines an angularly disposed opened ended cylindrical configuration.

An adjustment tab 15 extends from the annular band 10 at a point generally opposite said thumb engaging portion 14. Velcro ® fastening material V is secured and extends inwardly from the free end of said tab 15 facing said annular band 10. A registering path of velcro ® V1 is secured to the body of the annular band 10 in spaced relation to said point of attachment of said adjustable tab 15.

Velcro ® V and V1 are so positioned that said adjustable tab 15 can be secured to the band surface via the velcro ® at various points within the registration area of said velcro ® V1 to effectively tighten said annular band 10 on the patient's hand 11.

A secondary adjustable tab 16 is secured to and extends from said thumb engagement portion 14 having registering velcro ® material patches V2 and V3 on opposite sides thereof in staggered relationship from said end portion.

In use, the adjustable thumb restraint is first positioned on the patient's hand 11 with the annular band 10 engaging therearound with the patient's thumb 17 extending through the open ends of the thumb engaging portion 14. The secondary adjustable tab 16 is then wrapped around the thumb 17 and secured to itself via the velcro ® material patches V2 and V3 as hereinbefore described. The elongated tab 15 is then secured to its velcro ®* patch V1 stabilizing and tightening the annular band 10 on the patient's hand 11, thus a radial movement of the thumb 17 is restricted in the degree desired by the appropriate adjustment of the specific adjustment tabs 15 and 16. The advantage of a simple inexpensive and effective thumb restraint are self-evident when compared with the devices disclosed in prior art.

*Velcro is a Registered Trademark

Thus it will be seen that a new and useful thumb restraint has been illustrated and described and it will be obvious to those skilled in the art that various changes and modifications may be made therein without departing from the spirit of the invention, therefore I claim:

1. An adjustable thumb restraint for engagement on a person's hand, comprises a resilient annular band member, said band member having spaced parallel upper and lower edge portions, a thumb retaining sleeve secured to said annular band member, said sleeve extending both above and below said parallel edges of said annular band, an elongated adjustable tab extending from said sleeve, fastening means secured in oppositely disposed relation on said elongated tab inwardly from its free end, a secondary elongated adjustable tab secured to said annular band in spaced relation to said thumb receiving sleeve, fastening means secured said secondary elongated tab and said annular band for registration therewith.

2. The adjustable thumb restraint of claim 1 wherein said fastening means on said elongated tab is registrable on itself as said elongate tab is wrapped around said thumb retaining sleeve.

3. The adjustable thumb restraint of claim 1 wherein said fastening means is registrable with itself anywhere along its corresponding registering surface for integrated adjustment of said elongated tabs.

4. The adjustable thumb restraint of claim 1 wherein said thumb restraint sleeve is of a height equal to at least one-quarter the known longitudinal length of said annular band.

* * * * *